(12) United States Patent
Lemer et al.

(10) Patent No.: US 11,547,798 B2
(45) Date of Patent: Jan. 10, 2023

(54) INSTALLATION FOR THE INJECTION OF A RADIOACTIVE PRODUCT INTO A PATIENT AND METHOD FOR THE IMPLEMENTATION THEREOF

(71) Applicant: LEMER PROTECTION ANTI-X PAR ABREVIATION SOCIETE LEMER PAX, La Chapelle sur Erdre (FR)

(72) Inventors: Pierre-Marie Lemer, Nantes (FR); Xavier Setoain, Barcelona (ES)

(73) Assignee: LEMER PAX, La Chapelle sur Erdre (FR)

( * ) Notice: Subject to any disclaimer, the term of this patent is extended or adjusted under 35 U.S.C. 154(b) by 461 days.

(21) Appl. No.: 16/614,911

(22) PCT Filed: May 18, 2018

(86) PCT No.: PCT/EP2018/063158
§ 371 (c)(1),
(2) Date: Nov. 19, 2019

(87) PCT Pub. No.: WO2018/211092
PCT Pub. Date: Nov. 22, 2018

(65) Prior Publication Data
US 2020/0188584 A1    Jun. 18, 2020

(30) Foreign Application Priority Data

May 19, 2017 (FR) ........................................ 1754469

(51) Int. Cl.
*A61M 5/168* (2006.01)
*A61M 5/00* (2006.01)
(Continued)

(52) U.S. Cl.
CPC ........ *A61M 5/16827* (2013.01); *A61M 5/007* (2013.01); *A61M 5/1785* (2013.01);
(Continued)

(58) Field of Classification Search
CPC .............. A61M 5/16827; A61M 5/007; A61M 5/1785; A61M 2005/1403;
(Continued)

(56) References Cited

U.S. PATENT DOCUMENTS 6,767,319 B2    7/2004 Reilly et al.
2004/0006309 A1*    1/2004 Rusnak ................... A61D 1/025
604/131
(Continued)

FOREIGN PATENT DOCUMENTS

FR    2917981 A1    1/2009
WO    99/56117 A1    11/1999
(Continued)

OTHER PUBLICATIONS

International Search Report, dated Aug. 13, 2018, from corresponding PCT application No. PCT/EP2018/063158.

*Primary Examiner* — Lauren P Farrar
*Assistant Examiner* — Hamza A Darb
(74) *Attorney, Agent, or Firm* — Nixon & Vanderhye

(57) ABSTRACT

Disclosed is a system for injecting a radioactive product to a patient, wherein the system includes: a first syringe containing the radioactive product, whose plunger cooperates with an injection mass, acting by gravity, associated with deactivatable holding element; a mobile stop arranged to constitute an end-of-travel stop for the retraction of the plunger, as a function of the volume of radioactive product to be injected to the patient; a second syringe containing a rinsing product, whose plunger cooperates with a rinsing mass, acting by gravity, associated with deactivatable hold- (Continued)

ing element; a trigger control element for triggering the injection of the radioactive product to the patient; and a management element including a unit for displacing the mobile stop structure as a function of the prescribed activity to be injected to the patient, and a unit for controlling the deactivatable holding element of the masses.

20 Claims, 2 Drawing Sheets

(51) Int. Cl.
  *A61M 5/178* (2006.01)
  *A61M 5/14* (2006.01)
  *A61M 5/145* (2006.01)
(52) U.S. Cl.
  CPC ............... *A61M 2005/1403* (2013.01); *A61M 2205/0272* (2013.01); *A61M 2205/502* (2013.01); *A61M 2209/01* (2013.01)

(58) Field of Classification Search
  CPC .... A61M 2205/0272; A61M 2205/502; A61M 2209/01; A61M 5/1452
  See application file for complete search history.

(56) References Cited

U.S. PATENT DOCUMENTS

| | | | |
|---|---|---|---|
| 2011/0201867 A1* | 8/2011 | Wagner | G21F 5/018 600/5 |
| 2014/0276411 A1 | 9/2014 | Cowan et al. | |

FOREIGN PATENT DOCUMENTS

| | | |
|---|---|---|
| WO | 2008/037939 A2 | 4/2008 |
| WO | 2009/152320 A2 | 12/2009 |
| WO | 2010/039573 A2 | 4/2010 |

\* cited by examiner

INSTALLATION FOR THE INJECTION OF A RADIOACTIVE PRODUCT INTO A PATIENT AND METHOD FOR THE IMPLEMENTATION THEREOF

TECHNICAL FIELD TO WHICH THE INVENTION RELATES

The present invention relates to the general field of nuclear medicine. It more particularly relates to an installation for injecting a radioactive product to a patient as well as to the implementation method thereof.

TECHNOLOGICAL BACK-GROUND

Some medical imaging techniques (in particular, single-photon emission computed tomography, also called SPECT) use radioactive substances emitting ionizing radiations, called radiopharmaceuticals or radiotracers, that consist of a radioisotope associated with a vector adapted to selectively fix in the organism.

After injection of this radiotracer to the patient, the image of its distribution in the organism is taken, for example by means of a gamma-camera.

To limit the doses of radiation received by the patient and by the staff in charge of the handling, medical-use radioisotopes of short half-life, i.e. whose level of emitted radiation rapidly decreases with time, are used.

For example, such radiotracer elements are used for searching for the epileptogen focus in patients suffering from epileptic disorders.

For that purpose, a syringe containing the chosen SPECT cerebral perfusion agent (in particular, 99mTc-HMPAO or 99mTc-ECD) is prepared in advance, and an operator performs the injection at the onset of an epileptic seizure.

It is then essential to react very quickly and to inject the product very rapidly (in a few seconds), to obtain the most localized possible fixing of the radiotracer on the epileptogen focus, and consequently to obtain a very accurate image of this focus, in order, on the one hand, to confirm the possibility of a surgical intervention and, on the other hand, to localize at best the defective area of the brain to be surgically removed.

Moreover, ideally, it is proper to inject an accurate activity (or, by misuse of language, a dose) of this radiotracer, adapted to the patient, which is function of the camera sensitivity and of the human organ to be studied, to obtain the quality of image just necessary for a good diagnosis. It is to be noted that a too low injected activity may lead to the impossibility of reading the image obtained and hence to the necessity of performing the injection again. On the contrary, a too high activity may saturate the camera used (which also makes the diagnosis difficult), but above all it may lead to a useless over-exposure of the patient to the ionizing radiations.

However, as the epileptic seizures occur rather randomly, the urgency to intervene does not allow the operator to compute an accurate volume to be injected, taking into account the activity remaining in the syringe at that time (due to the rapid decrease of activity of the radioisotope). That is why, usually, the operator injects the whole syringe volume available, with the inherent risks in terms of patient over-exposure and of image quality.

Moreover, despite the type of product implemented (short half-life), another constraint to be taken into account relates to the radioprotection of the medical staff in charge of preparing the radiotracer dose and of injecting it to the patient.

Conventionally, the doses to be injected are taken into a syringe provided with a suitable shield, itself placed in a shielded enclosure equipped with suitable measurement and control means, allowing the wanted dose of radioactive product to be taken into the syringe. Then, an operator retrieves the shielded syringe and visits the patient to make the injection.

However, that way to proceed does not offer an optimum safety as regards the radioprotection for the operator or even for the patient.

Within this framework, the documents U.S. Pat. No. 6,767,319 and WO-2008-037939 describe radioactive product calibration and injection equipment aiming at limiting the staff exposure to the radioactive substance and also optimizing the patient safety.

The corresponding installations comprise—means for supporting an injectable radioactive product source,—means for supporting a syringe, which are equipped with means for automatic operation of the plunger thereof, and are associated with a device of the activity meter type for measuring in real time the radioisotopic activity emitted by the product contained in the syringe, and—a valve system that is hydraulically connected, through pipes, to the radioactive mother source, to the syringe, to a physiological serum source and to an injection catheter intended to be connected to the patient.

The radioactive product source and the syringe, in particular, are surrounded with a radioprotective material.

This equipment also comprises means intended to pilot the valve system and the syringe plunger operating means, in a suitable manner to ensure, in a first time, the sampling of a dose of radioactive product and/or of physiological serum into the syringe, and in a second time, the ejection, through the injection catheter, of the previously drawn radioactive product and/or physiological serum. The dose of radioactive product is measured by the activity meter during the sampling into the syringe.

But such installations are relatively complex; moreover, they do not allow a rapid injection of the product to the patient, in particular due to the means used for operating the syringe plunger.

Documents FR-2 917 981, WO-2010/039573 and US-2014/276411 still describe installations of the same type. Here again, the syringe plunger operating means consist of conventional actuators or motorizations that do not allow a rapid injection of the product to the patient.

OBJECT OF THE INVENTION

In order to remedy the above-mentioned drawback of the state of the art, the present invention proposes an installation for injecting a radioactive product to a patient, said system being of the type comprising:

a first syringe of vertical longitudinal axis, comprising a body provided with a tip and a plunger directed upward, said tip being connected to a patient injection means through an injection pipe, said first syringe body being adapted to contain said radioactive product to be injected, means for operating said first syringe plunger, means for determining continuously or on a regular basis the volume of radioactive product to be injected to the patient, taking into account a prescribed activity to be injected to the patient, trigger control means for triggering the injection of the radioactive product to the patient, and, according to the invention, such installation is characterized in that it comprises:

said means for operating said plunger of said first syringe, comprising an injection mass, adapted to be positioned above said plunger of said first syringe and adapted to press on said plunger by gravity, to ensure the injection of the radioactive product to the patient, said injection mass being associated with deactivatable holding means, which allow the holding thereof in inactive position for preventing said injection, and the release thereof to ensure said pressing on said plunger of said first syringe, a mobile stop structure operated by a stop motorization, said mobile stop structure being arranged to cooperate with said plunger of said first syringe and/or with said injection mass, so as, from a position of said plunger extracted from said first syringe body, to constitute an end-of-travel stop for the retraction of said plunger, as a function of the volume of radioactive product to be injected to the patient, means for detecting that said plunger of said first syringe has reached the end of travel, with respect to said mobile stop structure, a second syringe of vertical longitudinal axis, comprising a body provided with a tip and a plunger directed upward, said body of second syringe being adapted to contain a rinsing product, and said tip of second syringe being connected by a channel to said tip of said first syringe or to an upstream portion of said injection pipe, means for operating said plunger of said second syringe, comprising a rinsing mass, adapted to be positioned above said plunger of said second syringe, and adapted to press on said plunger by gravity, to ensure the at least partial rinsing of said pipe, said rinsing mass being associated with deactivatable holding means, which allow the holding thereof in inactive position for preventing said rinsing, and the release thereof to ensure said pressing on said plunger of said second syringe, management means comprising:

means for controlling said stop motorization in order to displace said mobile stop structure as a function of said prescribed activity to be injected to the patient, means for controlling said deactivatable holding means of said injection mass, means for controlling said deactivatable holding means of said rinsing mass.

Such a combination of characteristics allows a rapid and sure injection of the radioactive product.

Other non-limitative and advantageous characteristics of the installation according to the invention, taken individually or according to all the technically possible combinations, are the following:

said deactivatable holding means of said injection mass and said deactivatable holding means of said rinsing mass consist of electromagnets, and said injection and rinsing masses are made of a suitable material to allow the holding and releasing thereof by said electromagnets;

the installation comprises means for detecting the end of travel of said plunger of said second syringe;

the installation comprises a check valve downstream from the tip of said first syringe, adapted to prevent the backflow of fluid into said first syringe, as well as a check valve downstream from the tip of said second syringe, adapted to prevent the backflow of fluid into said second syringe;

the installation comprises:

a/ a mobile unit mounted on wheels, comprising:

said first syringe associated with said mobile stop operated by said stop motorization, said means for detecting the end of travel of its plunger, said injection mass and the deactivatable holding means thereof, said injection pipe and said patient injection means, said second syringe associated with said rinsing mass and the deactivatable holding means thereof, trigger control means for triggering the injection of the radioactive product to the patient, and a management automaton adapted for determining continuously or on a regular basis the volume of radioactive product to be injected to the patient, taking into account a prescribed activity to be injected to the patient, controlling said stop motorization in order to displace said mobile stop structure as a function of said prescribed activity to be injected to the patient, and controlling said deactivatable holding means of said injection mass, as well as said deactivatable holding means of said rinsing mass, a status setting and display screen, a receptacle made of an ionizing radiation protective material, in which is placed at least said first syringe, and b/ a remote-control box comprising trigger control means for triggering the injection of the radioactive product to the patient, and a status display screen.

The invention also proposes a method for implementing the installation described hereinabove, wherein said method consists in:

preparing said first syringe with its syringe body containing said radioactive product and said second syringe with its syringe body containing said rinsing product, and positioning them under said injection mass and under said rinsing mass, respectively, held by the respective holding means thereof, determining continuously or on a regular basis the volume of radioactive product intended to be injected to a patient, taking into account a prescribed target activity, and consequently displacing said mobile stop structure by means of said stop motorization, actuating said trigger control means, deactivating said deactivatable holding means of said injection mass, to release it and to ensure the pressing thereof on the plunger of said first syringe in order to ensure the supply of said injection pipe, after detection of the end of travel of said plunger of said first syringe, deactivating said deactivatable holding means of said rinsing mass, to release it and to ensure the pressing thereof on the plunger of said second syringe in order to make the rinsing of said injection pipe.

According to a particularly interesting application, the method consists in preparing said first syringe with its syringe body containing a cerebral perfusion radioactive agent adapted to localize an epileptogen focus in a patient.

DETAILED DESCRIPTION OF AN
EXEMPLARY EMBODIMENT

The following description with respect to the appended drawings, given by way of non-limitative examples, will permit a good understanding of what the invention consists in and of how it can be implemented.

INSTALLATION

Figure 1:
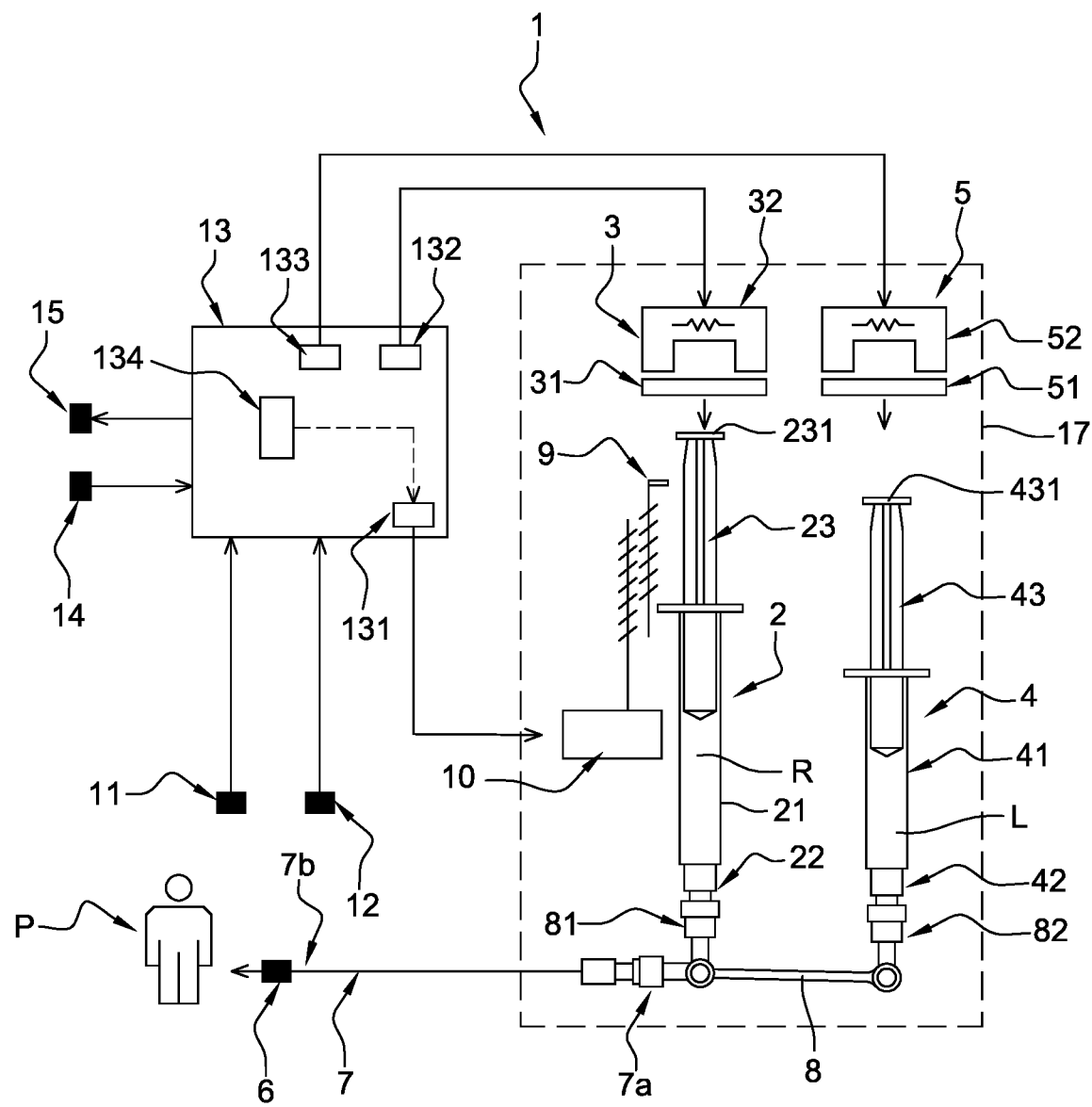
FIG. 1 is a schematic view of an installation according to the invention.

The installation 1 according to the invention shown in FIG. 1 comprises—a first syringe 2 of vertical longitudinal axis, comprising a body 21 provided with a tip 22 and a plunger 23 directed upward, wherein said first syringe 2 is associated with means 3 for operating the plunger 23 thereof, and—a second syringe 4 of vertical longitudinal axis, comprising a body 41 provided with a tip 42 and a plunger 43 directed upward, wherein said second syringe 4 is associated with means 5 for operating the plunger 43 thereof.

The body 21 of the first syringe 2 is intended to contain a radioactive product (radiotracer) R that is wanted to be injected to a patient P; and the tip 22 of this first syringe 2 is connected to a patient injection means 6 through an injection pipe 7. The tip 22 of the first syringe 2 is connected to an upstream portion 7a of the injection pipe 7; and the downstream portion 7b of this injection pipe 7 is connected to the patient injection means 6.

The body 41 of the second syringe 4 is adapted to contain a rinsing product L, and the tip 42 of this second syringe 4 is connected through a channel 8 to the upstream portion 7a of the injection pipe 7 (or to the tip 22 of said first syringe 2).

The means 3 for operating the plunger 23 of the first syringe 2 comprise an injection mass 31 adapted to press on said plunger 23 by gravity (more precisely, adapted to cooperate with the head 231 of the plunger 23), to ensure the injection of the radioactive product R to the patient P; this injection mass 31 is associated with deactivatable holding means 32, which allow the holding thereof in inactive position for preventing said injection, and the release thereof to ensure said pressing on the plunger 23 of said first syringe 2.

The injection mass 31 is held by its deactivatable holding means 32 above the plunger 23 of the first syringe 2, vertically aligned with the latter. In this case, this injection mass 31 is herein held by its deactivatable holding means 32 remote from the plunger 23, separated/spaced apart from the latter.

These deactivatable holding means 32 are in the form of an electromagnet. The injection mass 31 is a single-piece part or an assembly of parts, made of a suitable material (for example, stainless steel) adapted to allow the holding and releasing thereof by said electromagnet 32.

The means 5 for operating the plunger 43 of the second syringe 4 comprise a rinsing mass 51 adapted to press on said plunger 43 by gravity (more precisely, adapted to cooperate with the head 431 of the plunger 43), to ensure the at least partial rinsing of the injection pipe 7; this rinsing mass 51 is associated with deactivatable holding means 52, which allow the holding thereof in inactive position for preventing said rinsing, and the release thereof to ensure said pressing on said plunger 43 of said second syringe 4.

The rinsing mass 51 is held by its deactivatable holding means 52 above the plunger 43 of the first syringe 4, vertically aligned with the latter. In this case, this rinsing mass 51 is herein held by its deactivatable holding means 52 remote from the plunger 43, separated/spaced apart from the latter.

These deactivatable holding means 52 are in the form of an electromagnet. The rinsing mass 51 is a single-piece part or an assembly of parts, made of a suitable material (for example, stainless steel) adapted to allow the holding and releasing thereof by said electromagnet 52.

For example, the masses 31, 51 are held in place when the electromagnets 32, 52 are powered off and they are released only when the electromagnets 32, 52 are powered on.

The installation 1 also comprises a mobile stop structure 9 operated by a stop motorization 10, wherein said mobile stop structure 9 is arranged to cooperate with the plunger 23 of said first syringe 2 and/or with the injection mass 31, so as, from a position of said plunger 23 extracted from said first syringe body 21, to constitute an end-of-travel stop for the retraction of said plunger 23, as a function of the volume of radioactive product R that is wanted to be injected to the patient P.

This mobile stop structure 9 herein cooperates with the bottom of the injection mass 31. In a variant embodiment, it may cooperate with the bottom of the head 231 of the plunger 23 of the syringe 2.

The stop motorization 10 consists of a linear table, a motor and a reduction gear to improve the accuracy of the displacement.

The installation 1 also includes means 11 for detecting that the plunger 23 of said first syringe 2 has reached the end of travel, with respect to said mobile stop structure 9; these detection means 11 may consist of an electrical contact stop screw, cooperating with the injection mass 31.

It also includes means 12 for detecting that the plunger 43 of said second syringe 4 has reached the end of travel, with respect to the body 41 thereof; these detection means 12 may consist of an electrical contact stop screw, cooperating with the injection mass 51.

The operation of the installation 1 is managed by management means 13 in the form of a computing automaton, comprising:

means 131 for controlling the stop motorization 10, means 132 for controlling the deactivatable holding means 32 of the injection mass 31, means 133 for controlling the deactivatable holding means 52 of the rinsing mass 51, means 134 for determining continuously or on a regular basis the volume of radioactive product R to be injected to the patient, taking into account a prescribed activity to be injected to the patient.

For that purpose, these determination means 134 consist of computing means that take into account the initial activity introduced into the body 21 of the first syringe 2, the half-life of the radioisotope in presence and the time elapsed between, on the one hand, the time of filling the syringe body 21 with the radioactive product R and, on the other hand, the time of injection to the patient.

The corresponding computation may be performed continuously or on a regular basis, for example every 30 seconds, every minute or other.

Starting from the computed activity present in the body 21 of the syringe 2, the automaton 13 controls the stop motorization 10, continuously or on a regular basis, to displace the mobile stop structure 9 as a function of the volume of product R to be injected to the patient corresponding to the prescribed activity.

This allows injecting to the patient the prescribed activity, whatever the moment of the injection with respect to the initial moment of preparation of the syringe.

The installation 1 also includes trigger control means 14 for triggering the injection of the radioactive product R to the patient. These trigger control means 14 consist of at least one pushbutton intended to be actuated by an operator; preferably, the system includes two pushbuttons intended to be simultaneously operated, to avoid the unintentional triggering events.

Still preferably, these trigger control means 14 are doubled and comprise:

first trigger control means (advantageously in the form of two pushbuttons) arranged on a mobile unit integrating the injection syringes 2 and 4, the means 3, 5 for controlling their plungers 23, 43 and the injection pipe 7, this mobile unit being intended to be placed next to the patient P, and second trigger control means (also advantageously in the form of two pushbuttons) arranged on a remote-control box, allowing an operator to control the injection triggering remote from the patient (and hence remote from the radioactive source).

Safety means are advantageously provided (managed by the automaton 13), adapted to prevent the injection of the radiotracer R to the patient, in particular in the case where the activity remaining in the syringe body 21 is lower than the activity prescribed for the patient, or also if the product R to be injected is considered as being outdated.

The installation also advantageously includes a sound alarm 15 adapted to be activated all along the injection operation, i.e. from the injection command order to the end of the rinsing injection.

As can be seen in FIG. 1, a check valve 81 is provided downstream from the tip 22 of the first syringe 2, adapted to prevent the backflow of fluid towards the first syringe 2. Likewise, a check valve 82 is provided downstream from the tip 42 of the second syringe 4 to prevent the backflow of fluid towards the second syringe 4.

On the other hand, the installation includes means for protecting the environment and, in particular, the operator(s) and the patient, against the ionizing radiations emitted by the radiotracer R.

For that purpose, at least the first syringe 2 is placed in a receptacle 17 made of an ionizing radiation protective material, for example a 4-mm-thick lead receptacle.

The management automaton 13 is configured and set to implement the different functionalities described hereinabove. It is associated with a human-machine interface, having a display screen, adapted for inputting all the parameters necessary for the implementation thereof, as a function of the contemplated application.

Figure 2:
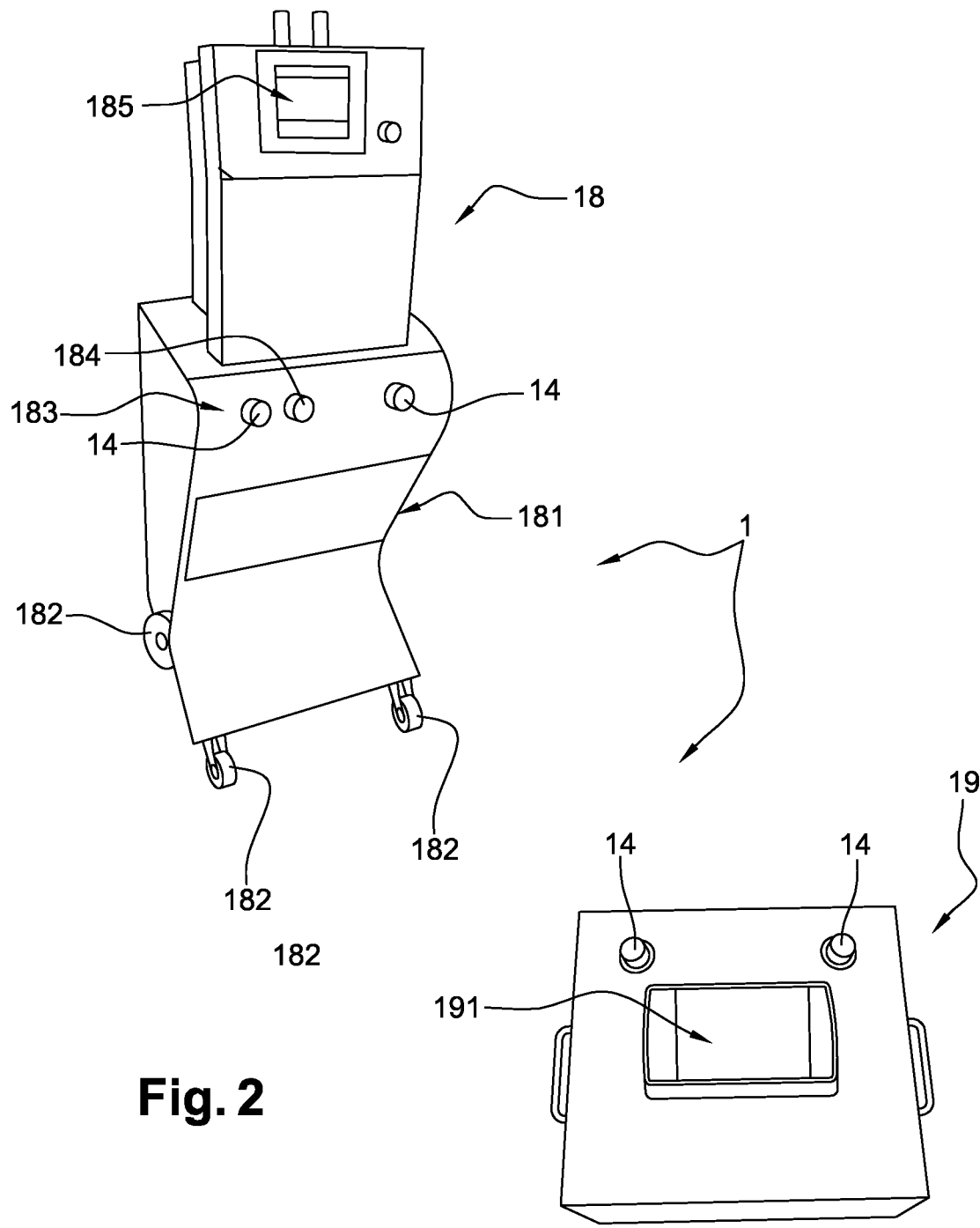
FIG. 2 is a perspective view of the external structure of a possible embodiment of the installation illustrated in FIG. 1.

FIG. 2 illustrates a possible structural configuration of the injection installation 1.

In this embodiment, the injection system 1 comprises, on the one hand, a mobile unit 18 and, on the other hand, a remote-control box 19.

The mobile unit 18 consists of a kind of case 181 mounted on wheels 182, which comprises the whole means for ensuring the injection of the radiotracer R to the patient P, as well as the means that allow the secured management of this injection.

This mobile unit 18 hence comprises different inner equipment devices that do not appear in FIG. 2, i.e.: the first syringe 2 containing the radiotracer R, the mobile stop 9 operated by the stop motorization 10, the means 11 for detecting the end of travel of the syringe plunger 23, the injection mass 31 and the deactivatable holding means 32 thereof, the second syringe 4 containing the rinsing product L, the rinsing mass 51 and the deactivatable holding means 52 thereof, at least the syringe 2 being placed in a radio-protected receptable (for example, a 4-mm-thick lead receptacle).

It also comprises:

the injection pipe 7 and the injection means 6 (for example, an intravenous needle), not shown, the management automaton 13 (not visible), a manual control panel 183 with two control pushbuttons 14 for triggering the injection of the radioactive product R to the patient and an on/off button 184, a status setting and display screen 185.

The remote-control box 19 comprises two control pushbuttons 14 for triggering the injection of the radiotracer R to the patient, and a status display screen 191.

Method

The installation 1 is particularly intended for injection of cerebral perfusion agents. It allows in particular computing the volume of radiotracer R to inject in a few seconds (for example, less than 6 seconds) a cerebral perfusion agent for localizing an epileptogen focus, while preserving the operators from exposure to ionizing radiations.

The method for implementing this installation 1 comprises the following operations:

a/ Making the different tests regarding the functional state of the installation, in particular the power supply thereof and the upper positioning of the injection 31 and rinsing 51 masses (distant positioning from the syringe plungers 23, 43);

b/ Preparing the first syringe 2 with its syringe body 21 containing the suitable radiotracer R, for example 8 ml of a mixture HMPAO+99mTc having an activity of 950 MBq, and preparing the second syringe 4 with its syringe body 41 containing the rinsing product L, for example 5 ml of sodium chloride (NaCl); then, positioning these two syringes under the injection mass 31 and under the rinsing mass 51, respectively, held by the respective holding means 32, 52 thereof;

c/ Initializing the installation by pressing on the on/off pushbutton 184;

d/ Verifying the general parameters of the equipment, in particular the date and hour of the system;

e/ Possibly authenticating the operator by inputting a password;

f/ Inputting the patient identification parameters (name, surname, birth date), the parameters linked to the radiotracer R (prepared activity, nature of the radiotracer, date and hour of preparation) and parameters linked to the prescription (prescribed activity, name of the preparator . . . );

g/ Once this information correctly filled in, the computing automaton controls the displacement of the mobile stop structure 9 to take its suitable position as a function of the prescribed activity, the prepared activity, the date of preparation and the current date;

A timer is triggered to compute the remaining activity in the first syringe 2 and to verify the expiry of the product;

Subsequently, the computing automaton determines continuously and on a regular basis the volume of radioactive product R to be injected to the patient, taking into account the prescribed target activity intended to be injected to the patient, and it consequently displaces the mobile stop structure 9 by means of the stop motorization 10 (for example, every 90 seconds);

h/ In the hypothesis in which the syringe 2 already filled with the radiotracer R does no longer contain enough activity, and/or the radiotracer R has exceeded its expiry date, the equipment informs the operator about it and it is then necessary to replace the radiotracer R and to record the new data;

i/ At the onset of a seizure in the patient: the operator operates the means for controlling the injection of the radiotracer R, by simultaneous pressing, either on the two pushbuttons 14 of the mobile unit 18, or (preferably) on the two pushbuttons 14 of the remote-control box 19;

j/ The deactivatable holding means 32 of the injection mass 31 are deactivated for releasing it and ensuring the pressing thereof on the plunger 23 of the first syringe 2 in order to supply the injection pipe 7 and to inject the radiotracer R to the patient P;

k/ After detection of the end of travel of the plunger 23 of the first syringe 2 (for example, by contact of the injection mass 31 with the injection end-of-travel detector 11), the control means 52 of the rinsing mass 51 are deactivated, to release it and to ensure the pressing thereof on the plunger 43 of the second syringe 4 in order to ensure the rinsing of the injection pipe 7 and to ensure the injection of the totality of the activity prescribed to the patient P;

The end of the rinsing step is detected by contact of the rinsing mass 51 with the rinsing end-of-travel detector 12);

l/ Once the injection performed, the operator goes back near the mobile unit to use the saving and resetting functions. The injection data and the patient data may be saved on an external support;

m/ The injection and rinsing masses 31, 51 must be manually replaced in upper position to allow the starting of a new cycle.

At the starting of injection of the radiotracer R and at the starting of injection of the rinsing product, timers are triggered, stopped upon detection of end of travel of the plungers 23, 43, to know the injection times. Suitable alarms 15 are also activated during these injections (a same alarm for the injections of radiotracer R and of rinsing product L, or two different alarms).

Such an installation structure allows a very rapid injection of radiotracer to the patient (of the order of a few seconds, for example in less than 6 seconds), and in a very secured manner, both for the operators and for the patients.

Once the radiotracer R injected to the patient, it fixes on the most active areas of the brain and in particular the area responsible of the epileptic seizure. The hospital staff has then about 3 h to take the patient to the acquisition room to image the brain by means of a gamma-camera.

The invention claimed is:

1. An installation for injecting a radioactive product to a patient, said installation comprising:
 a first syringe of vertical longitudinal axis, the first syringe comprising a body provided with a tip and a plunger directed upward, said tip being connected to a patient injector through an injection pipe, said first syringe body being configured to contain said radioactive product to be injected;
 a first plunger operator system configured to operate said first syringe plunger, the first plunger operator system comprising an injection mass configured to be positioned above the first syringe plunger and configured to press on the first syringe plunger by gravity, to ensure injection of the radioactive product to the patient, the injection mass being associated with a first deactivatable holder to allow holding thereof in an inactive position to prevent the injection and to allow a release thereof to ensure the pressing on the first syringe plunger;
 a computer configured to continuously or regularly determine the volume of radioactive product to be injected to the patient, taking into account a prescribed activity to be injected to the patient;
 a first trigger controller configured to trigger the injection of the radioactive product to the patient;
 a mobile stop structure operated by a stop motorization, said mobile stop structure being configured to cooperate with one or more of: (i) said first syringe plunger, and (ii) said injection mass to constitute an end of travel stop for retraction of said first syringe plunger from a position of the first syringe plunger extracted from the first syringe body, as a function of the volume of radioactive product to be injected to the patient;
 a first detector configured to detect that said first syringe plunger reached the end of travel, with respect to said mobile stop structure;
 a second syringe of vertical longitudinal axis, the second syringe comprising a body provided with a tip and a plunger directed upward, said second syringe body being configured to contain a rinsing product, said second syringe tip being connected by a channel to said first syringe tip or to an upstream portion of said injection pipe; and
 a second plunger operator system configured to operate said second syringe plunger, the second plunger operator system comprising a rinsing mass configured to be positioned above said second syringe plunger and to press on said second syringe plunger by gravity, to ensure at least partial rinsing of said injection pipe, said rinsing mass being associated with a second deactivatable holder to allow holding thereof in an inactive position to prevent said rinsing and to allow a release thereof to ensure said pressing on said second syringe plunger,
 wherein the computer is configured to:
  control said stop motorization in order to displace said mobile stop structure as a function of said prescribed activity to be injected to the patient,
  control said first deactivatable holder of said injection mass, and
  control said second deactivatable holder of said rinsing mass.

2. The installation according to claim 1, wherein said first deactivatable holder of said injection mass and said second deactivatable holder of said rinsing mass consist of electromagnets, and said injection mass and the rinsing mass are made of a material configured to allow the holding and the releasing thereof by said electromagnets.

3. The installation according to claim 2, further comprising a second detector configured to detect that said second syringe plunger reached the end of travel.

4. The installation according to claim 3, further comprising:
 a first check valve downstream from the tip of said first syringe, the first check valve being configured to prevent a backflow of fluid into said first syringe, and
 a second check valve downstream from the tip of said second syringe, the second check valve being configured to prevent a backflow of fluid into said second syringe.

5. The installation according to claim 3, further comprising:
 a mobile unit mounted on wheels, the mobile unit comprising:
  said first syringe associated with said mobile stop structure operated by said stop motorization, the first detector configured to detect the end of travel of the first syringe plunger,
said injection mass,
the first deactivatable holder,
said injection pipe,
said patient injector,
said second syringe associated with said rinsing mass and the second deactivatable holder,
the first trigger controller configured to trigger the injection of the radioactive product to the patient,
the computer,
a status setting and display screen,
a receptacle made of an ionizing radiation protective material, the receptacle being configured to receive at least said first syringe; and
a remote-control box comprising
a second trigger controller configured to trigger the injection of the radioactive product to the patient, and
a status display screen.

6. The installation according to claim 2, further comprising:
a first check valve downstream from the tip of said first syringe, the first check valve being configured to prevent a backflow of fluid into said first syringe, and
a second check valve downstream from the tip of said second syringe, the second check valve being configured to prevent a backflow of fluid into said second syringe.

7. The installation according to claim 6, further comprising:
a mobile unit mounted on wheels, the mobile unit comprising:
said first syringe associated with said mobile stop structure operated by said stop motorization,
the first detector configured to detect the end of travel of the first syringe plunger,
said injection mass,
the first deactivatable holder,
said injection pipe,
said patient injector,
said second syringe associated with said rinsing mass and the second deactivatable holder,
the first trigger controller configured to trigger the injection of the radioactive product to the patient,
the computer,
a status setting and display screen,
a receptacle made of an ionizing radiation protective material, the receptacle being configured to receive at least said first syringe; and
a remote-control box comprising
a second trigger controller configured to trigger the injection of the radioactive product to the patient, and
a status display screen.

8. The installation according to claim 2, further comprising:
a mobile unit mounted on wheels, the mobile unit comprising:
said first syringe associated with said mobile stop structure operated by said stop motorization,
the first detector configured to detect the end of travel of the first syringe plunger,
said injection mass,
the first deactivatable holder,
said injection pipe,
said patient injector,
said second syringe associated with said rinsing mass and the second deactivatable holder,
the first trigger controller configured to trigger the injection of the radioactive product to the patient,
the computer,
a status setting and display screen,
a receptacle made of an ionizing radiation protective material, the receptacle being configured to receive at least said first syringe; and
a remote-control box comprising
a second trigger controller configured to trigger the injection of the radioactive product to the patient, and
a status display screen.

9. A method for implementing the installation according to claim 2, the method comprising:
preparing said first syringe with the first syringe body containing said radioactive product and said second syringe with the second syringe body containing said rinsing product, and positioning the first syringe and the second syringe under said injection mass and under said rinsing mass, respectively, held by the respective first and second holders thereof;
continuously or regularly determining the volume of radioactive product intended to be injected to the patient, taking into account the prescribed target activity, and consequently displacing said mobile stop structure by said stop motorization;
actuating said first trigger controller;
deactivating said first deactivatable holder of said injection mass, to release the injection mass and to ensure the pressing thereof on the first syringe plunger in order to supply said injection pipe; and
after detecting the end of travel of said first syringe plunger, deactivating said second deactivatable holder of said rinsing mass, to release the rinsing mass and to ensure the pressing thereof on the second syringe plunger in order to make the rinsing of said injection pipe.

10. The installation according to claim 1, further comprising a second detector configured to detect that said second syringe plunger reached an end of travel.

11. The installation according to claim 10, further comprising:
a first check valve downstream from the tip of said first syringe, the first check valve being configured to prevent a backflow of fluid into said first syringe, and
a second check valve downstream from the tip of said second syringe, the second check valve being configured to prevent a backflow of fluid into said second syringe.

12. The installation according to claim 11, further comprising:
a mobile unit mounted on wheels, the mobile unit comprising:
said first syringe associated with said mobile stop structure operated by said stop motorization,
the first detector configured to detect the end of travel of the first syringe plunger,
said injection mass,
the first deactivatable holder,
said injection pipe,
said patient injector,
said second syringe associated with said rinsing mass and the second deactivatable holder,
the first trigger controller configured to trigger the injection of the radioactive product to the patient, the computer,
a status setting and display screen,
a receptacle made of an ionizing radiation protective material, the receptacle being configured to receive at least said first syringe; and
a remote-control box comprising
a second trigger controller configured to trigger the injection of the radioactive product to the patient, and
a status display screen.

13. The installation according to claim 10, further comprising:
a mobile unit mounted on wheels, the mobile unit comprising:
said first syringe associated with said mobile stop structure operated by said stop motorization,
the first detector configured to detect the end of travel of the first syringe plunger,
said injection mass,
the first deactivatable holder,
said injection pipe,
said patient injector,
said second syringe associated with said rinsing mass and the second deactivatable holder,
the first trigger controller configured to trigger the injection of the radioactive product to the patient,
the computer,
a status setting and display screen,
a receptacle made of an ionizing radiation protective material, the receptacle being configured to receive at least said first syringe; and
a remote-control box comprising
a second trigger controller configured to trigger the injection of the radioactive product to the patient, and
a status display screen.

14. A method for implementing the installation according to claim 10, the method comprising:
preparing said first syringe with the first syringe body containing said radioactive product and said second syringe with the second syringe body containing said rinsing product, and positioning the first syringe and the second syringe under said injection mass and under said rinsing mass, respectively, held by the respective first and second holders thereof;
continuously or regularly determining the volume of radioactive product intended to be injected to the patient, taking into account the prescribed target activity, and consequently displacing said mobile stop structure by said stop motorization;
actuating said first trigger controller;
deactivating said first deactivatable holder of said injection mass, to release the injection mass and to ensure the pressing thereof on the first syringe plunger in order to supply said injection pipe; and
after detecting the end of travel of said first syringe plunger, deactivating said second deactivatable holder of said rinsing mass, to release the rinsing mass and to ensure the pressing thereof on the second syringe plunger in order to make the rinsing of said injection pipe.

15. The installation according to claim 1, further comprising:
a first check valve downstream from the tip of said first syringe, the first check valve being configured to prevent a backflow of fluid into said first syringe, and
a second check valve downstream from the tip of said second syringe, the second check valve being configured to prevent a backflow of fluid into said second syringe.

16. The installation according to claim 15, further comprising:
a mobile unit mounted on wheels, the mobile unit comprising:
said first syringe associated with said mobile stop structure operated by said stop motorization,
the first detector configured to detect the end of travel of the first syringe plunger,
said injection mass,
the first deactivatable holder,
said injection pipe,
said patient injector,
said second syringe associated with said rinsing mass and the second deactivatable holder,
the first trigger controller configured to trigger the injection of the radioactive product to the patient,
the computer,
a status setting and display screen,
a receptacle made of an ionizing radiation protective material, the receptacle being configured to receive at least said first syringe; and
a remote-control box comprising
a second trigger controller configured to trigger the injection of the radioactive product to the patient, and
a status display screen.

17. A method for implementing the installation according to claim 15, the method comprising:
preparing said first syringe with the first syringe body containing said radioactive product and said second syringe with the second syringe body containing said rinsing product, and positioning the first syringe and the second syringe under said injection mass and under said rinsing mass, respectively, held by the respective first and second holders thereof;
continuously or regularly determining the volume of radioactive product intended to be injected to the patient, taking into account the prescribed target activity, and consequently displacing said mobile stop structure by said stop motorization;
actuating said first trigger controller;
deactivating said first deactivatable holder of said injection mass, to release the injection mass and to ensure the pressing thereof on the first syringe plunger in order to supply said injection pipe; and
after detecting the end of travel of said first syringe plunger, deactivating said second deactivatable holder of said rinsing mass, to release the rinsing mass and to ensure the pressing thereof on the second syringe plunger in order to make the rinsing of said injection pipe.

18. The installation according to claim 1, further comprising:
a mobile unit mounted on wheels, the mobile unit comprising:
said first syringe associated with said mobile stop structure operated by said stop motorization,
the first detector configured to detect the end of travel of the first syringe plunger,
said injection mass,
the first deactivatable holder,
said injection pipe,
said patient injector, said second syringe associated with said rinsing mass and the second deactivatable holder, the first trigger controller configured to trigger the injection of the radioactive product to the patient, the computer, a status setting and display screen, a receptacle made of an ionizing radiation protective material, the receptacle being configured to receive at least said first syringe; and a remote-control box comprising a second trigger controller configured to trigger the injection of the radioactive product to the patient, and a status display screen.

19. A method for implementing the installation according to claim 1, the method comprising:

preparing said first syringe with the first syringe body containing said radioactive product and said second syringe with the second syringe body containing said rinsing product, and positioning the first syringe and the second syringe under said injection mass and under said rinsing mass, respectively, held by the respective first and second holders thereof;

continuously or regularly determining the volume of radioactive product intended to be injected to the patient, taking into account the prescribed target activity, and consequently displacing said mobile stop structure by said stop motorization;

actuating said first trigger controller;

deactivating said first deactivatable holder of said injection mass, to release the injection mass and to ensure the pressing thereof on the first syringe plunger in order to supply said injection pipe; and after detecting the end of travel of said first syringe plunger, deactivating said second deactivatable holder of said rinsing mass, to release the rinsing mass and to ensure the pressing thereof on the second syringe plunger in order to make the rinsing of said injection pipe.

20. The method according to claim 19, further comprising preparing said first syringe with the first syringe body containing a cerebral perfusion radioactive agent configured to localize an epileptogen focus in the patient.

* * * * *